United States Patent
Kishi et al.

(10) Patent No.: US 9,546,334 B2
(45) Date of Patent: Jan. 17, 2017

(54) REFRIGERATING MACHINE OIL, AND WORKING FLUID COMPOSITION FOR REFRIGERATING MACHINE WHICH IS PRODUCED USING SAME

(71) Applicant: KH NEOCHEM CO., LTD., Tokyo (JP)

(72) Inventors: Junya Kishi, Yokkaichi (JP); Yuichiro Nakai, Ichihara (JP); Tomohiro Iwasa, Yokkaichi (JP); Toshihiro Inayama, Yokkaichi (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 14/896,949

(22) PCT Filed: Jul. 31, 2014

(86) PCT No.: PCT/JP2014/070220
§ 371 (c)(1),
(2) Date: Dec. 9, 2015

(87) PCT Pub. No.: WO2015/016314
PCT Pub. Date: Feb. 5, 2015

(65) Prior Publication Data
US 2016/0168500 A1 Jun. 16, 2016

(30) Foreign Application Priority Data
Jul. 31, 2013 (JP) .................... 2013-159304

(51) Int. Cl.
C10M 105/38 (2006.01)
C09K 5/04 (2006.01)
C10M 171/00 (2006.01)
C07C 69/33 (2006.01)

(52) U.S. Cl.
CPC ............ C10M 105/38 (2013.01); C07C 69/33 (2013.01); C09K 5/045 (2013.01); C10M 171/008 (2013.01); C09K 2205/102 (2013.01); C09K 2205/104 (2013.01); C09K 2205/126 (2013.01); C09K 2205/24 (2013.01); C10M 2207/2835 (2013.01); C10M 2215/223 (2013.01); C10N 2220/028 (2013.01); C10N 2220/302 (2013.01); C10N 2230/06 (2013.01); C10N 2230/10 (2013.01); C10N 2230/70 (2013.01); C10N 2240/30 (2013.01)

(58) Field of Classification Search
CPC .. C10M 105/38; C10M 171/008; C09K 5/045; C09K 2205/126; C09K 2205/24; C10N 2040/30; B60H 1/3214; F25B 31/002; F25B 31/004; F25B 43/02; F25B 2500/16
USPC ..................... 252/68; 62/84, 468
See application file for complete search history.

(56) References Cited

U.S. PATENT DOCUMENTS

| | | | |
|---|---|---|---|
| 8,318,040 B2 | 11/2012 | Sawada et al. | |
| 2010/0038582 A1 | 2/2010 | Shimomura et al. | |
| 2010/0038583 A1 | 2/2010 | Shimomura et al. | |
| 2010/0051854 A1 | 3/2010 | Sawada et al. | |
| 2011/0247578 A1 | 10/2011 | Jansson et al. | |
| 2012/0024007 A1 | 2/2012 | Ota et al. | |
| 2012/0068104 A1 | 3/2012 | Rached et al. | |
| 2014/0100149 A1 | 4/2014 | Jansson et al. | |
| 2014/0374647 A1 | 12/2014 | Saito et al. | |
| 2015/0090921 A1* | 4/2015 | Kishi ............. | C07C 69/33 252/68 |

FOREIGN PATENT DOCUMENTS

| | | |
|---|---|---|
| DE | 10239134 A1 | 1/2003 |
| JP | 8109299 | 4/1996 |
| JP | 2001-107067 A | 4/2001 |
| JP | 2001107067 A * | 4/2001 |
| JP | 2002-129177 A | 5/2002 |
| JP | 2003-041275 | 2/2003 |
| JP | 3429031 | 5/2003 |
| JP | 2009-074017 A | 4/2009 |

(Continued)

OTHER PUBLICATIONS

English translation of WO 2013/141008, published Sep. 26, 2013.*
Search Report and Written Opinion in International Application No. PCT/JP2014/070220 dated Nov. 4, 2014.

Primary Examiner — Douglas Mc Ginty
(74) Attorney, Agent, or Firm — Marshall, Gerstein & Borun LLP

(57) ABSTRACT

Provided is a refrigerating machine oil which comprises an ester between a polyol consisting of at least one of pentaerythritol and dipentaerythritol represented by formula (I) and 2-propylheptanoic acid, and is characterized in that the refrigerating machine oil can be used in combination with a refrigerant consisting of 1,3,3,3-tetrafluoropropene (HFO-1234ze). When the refrigerating machine oil is used in combination with a refrigerant consisting of HFO-1234ze, excellent miscibility with the refrigerant, lubricity, thermal and chemical stability and the like can be achieved.

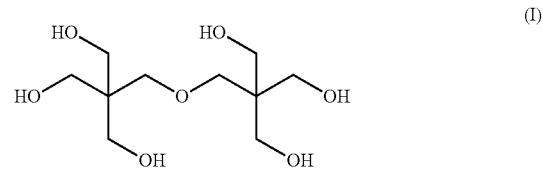

(I)

3 Claims, No Drawings

(56) References Cited

FOREIGN PATENT DOCUMENTS

| JP | 2011-085275 A | 4/2011 | | |
|----|---------------|--------|---|---|
| JP | 2012-031239 A | 2/2012 | | |
| JP | 2012-062469 A | 3/2012 | | |
| JP | 2012-506942 A | 3/2012 | | |
| JP | 2013-133443 A | 7/2013 | | |
| JP | WO 2013115296 A1 * | 8/2013 | ............ | C09K 5/041 |
| JP | WO 2013141008 A1 * | 9/2013 | ............ | C07C 69/33 |
| WO | WO-2008/117657 A1 | 10/2008 | | |
| WO | WO-2010/050871 A1 | 5/2010 | | |

* cited by examiner

REFRIGERATING MACHINE OIL, AND WORKING FLUID COMPOSITION FOR REFRIGERATING MACHINE WHICH IS PRODUCED USING SAME

TECHNICAL FIELD

The present invention relates to a refrigerating machine oil for 1,3,3,3-tetrafluoropropene (hereinafter, referred to as "HFO-1234ze") and a working fluid composition for a refrigerating machine using the refrigerating machine oil.

BACKGROUND ART

Recently, hydrofluorocarbon(s) (HFC), which has zero ozone-depletion potential, has been used as a refrigerant for a refrigerating machine and the like. However, HFC has high global-warming potential (GWP), and hence has been required to be replaced with a refrigerant with low GWP. A fluoropropene refrigerant, HFO-1234ze, has been considered as one of the candidates (Patent Literature 1).

A refrigerant-circulation cycle of a refrigerating machine or the like generally has a structure in which a refrigerating machine oil for lubricating a refrigerant compressor is circulated together with a refrigerant in the cycle. For this reason, a refrigerating machine oil is required to have miscibility with the refrigerant (refrigerant miscibility). In addition, since the refrigerating machine oil is used to lubricate the operational parts of a refrigerating machine, the lubricity is, of course, important. When phase separation of the refrigerant and the refrigerating machine oil occurs, the refrigerating machine oil discharged from the refrigerant compressor tends to build up in the cycle. As a result, problems such as a lubrication failure due to decrease in amount of the refrigerating machine oil in the refrigerant compressor and clogging of an expansion mechanism such as a capillary may occur (Patent Literatures 2 and 3).

On the other hand, when a refrigerating machine oil has a good miscibility with a refrigerant, the refrigerant is dissolved in the refrigerating machine oil in a refrigerant-circulation cycle, so that the viscosity (refrigerant solution viscosity) of a fluid composition which is a mixture of the refrigerating machine oil and the refrigerant decreases, making it difficult to retain the oil film necessary for the lubrication. For this reason, a problem of lubrication failure may arise. Especially, since a refrigerant consisting of HFO-1234ze (hereinafter, referred to as "HFO-1234ze refrigerant") has an extremely high miscibility with a refrigerating machine oil, the decrease in the refrigerant solution viscosity is remarkable. Note that it is possible to increase the viscosity of the refrigerating machine oil as a method for improving the lubricity. However, this is not preferable from the viewpoint of energy-saving (Patent Literature 4).

In addition, a refrigerating machine oil is required to have a high thermal and chemical stability enough to be used for a long period in the presence of a refrigerant. The HFO-1234ze refrigerant, which has an unsaturated bond, undergoes oxidative decomposition to generate an acid, and further the generated acid promotes hydrolysis of the refrigerating machine oil. For this reason, thermal and chemical stability of the refrigerating machine oil in a state where air or water is contained is especially important.

Each of Patent Literatures 1 and 5 discloses a refrigerating machine oil comprising an ester of a polyol and a fatty acid having 5 to 9 carbon atoms used in combination with a refrigerant containing HFO-1234ze. However, none of Patent Literatures 1 and 5 describe or suggest specific miscibility with the HFO-1234ze refrigerant, lubricity, or thermal and chemical stability.

Patent Literature 4 describes a refrigerating machine oil comprising an ester between pentaerythritol and a fatty acid B in which the ratio of branched fatty acids having 10 to 13 carbon atoms is 98.0% by mole. However, Patent Literature 4 does not disclose specific components of the branched fatty acids having 10 to 13 carbon atoms constituting the ester. In addition, Patent Literature 4 neither describes nor suggests specific miscibility with the HFO-1234ze refrigerant, thermal and chemical stability, lubricity, or the like.

Patent Literature 6 describes a tetraester between 2-propylheptanoic acid and pentaerythritol as a lubricant base stock for an automotive, an aeronautic or the like engine or turbine. However, Patent Literature 6 neither describes nor suggests the miscibility with refrigerant, the lubricity, or the thermal and chemical stability of the ester in the presence of the HFO-1234ze refrigerant.

CITATION LIST

Patent Literatures

Patent Literature 1: Japanese Patent Application Publication No. 2012-31239
Patent Literature 2: Japanese Patent Application Publication No. 2002-129177
Patent Literature 3: Japanese Patent No. 3429031
Patent Literature 4: International Publication No. WO2008/117657
Patent Literature 5: Japanese Patent Application Publication No. 2009-74017
Patent Literature 6: International Publication No. WO2010/050871

SUMMARY OF INVENTION

Technical Problems

An object of the present invention is to provide a refrigerating machine oil for an HFO-1234ze refrigerant excellent in miscibility with the refrigerant, lubricity, thermal and chemical stability, and the like, and a working fluid composition for a refrigerating machine using the refrigerating machine oil.

Solution to Problems

The present invention provides the following [1] and [2]:

[1] A refrigerating machine oil to be used in combination with a refrigerant consisting of HFO-1234ze, the refrigerating machine oil comprising an ester between a polyol consisting of at least one of pentaerythritol and dipentaerythritol represented by formula (I):

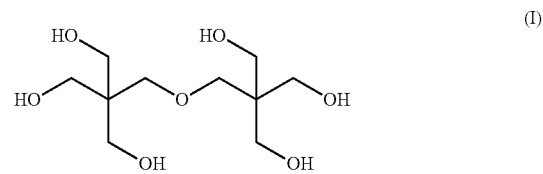 [SMILES: OCC(CO)(CO)COCC(CO)(CO)CO]

and 2-propylheptanoic acid.

[2] A working fluid composition for a refrigerating machine, the working fluid composition comprising:
an ester between a polyol consisting of at least one of pentaerythritol and dipentaerythritol represented by formula (I):
and 2-propylheptanoic acid; and
a refrigerant consisting of HFO-1234ze.

Advantageous Effects of Invention

The present invention makes it possible to provide a refrigerating machine oil which, when used in combination with an HFO-1234ze refrigerant, is excellent in miscibility with the refrigerant, lubricity, thermal and chemical stability, and the like, and a working fluid composition for a refrigerating machine using the refrigerating machine oil.

DESCRIPTION OF EMBODIMENTS

A refrigerating machine oil of the present invention comprises an ester between pentaerythritol and 2-propylheptanoic acid, an ester between dipentaerythritol represented by the above-described formula (I) (hereinafter, simply referred to as "dipentaerythritol") and 2-propylheptanoic acid, or a mixture of an ester between pentaerythritol and 2-propylheptanoic acid and an ester between dipentaerythritol and 2-propylheptanoic acid, and is characterized in that the refrigerating machine oil of the present invention is used in combination with an HFO-1234ze refrigerant.

Meanwhile, a working fluid composition for a refrigerating machine of the present invention comprises the refrigerating machine oil of the present invention and an HFO-1234ze refrigerant.

Hereinafter, an ester between pentaerythritol and 2-propylheptanoic acid, an ester between dipentaerythritol and 2-propylheptanoic acid, and a mixture of an ester between pentaerythritol and 2-propylheptanoic acid and an ester between dipentaerythritol and 2-propylheptanoic acid are referred to as an ester according to the present invention.

The ester according to the present invention is an ester whose constituent carboxylic acid is 2-propylheptanoic acid alone. Hence, when used as a base oil of a refrigerating machine oil for an HFO-1234ze refrigerant, the ester according to the present invention is excellent in miscibility with the HFO-1234ze refrigerant and moreover is excellent in lubricity and thermal and chemical stability in the presence of the HFO-1234ze refrigerant.

In addition, the ester according to the present invention may contain, as impurities, partial esters in which some of the hydroxy groups of pentaerythritol and/or dipentaerythritol are not esterified but remain as they are. If the amount of the hydroxy groups remaining in the ester is large, non-preferable phenomena occur such as a phenomenon in which a refrigerating machine oil turns cloudy at low temperature, and causes clogging of a capillary device of the refrigeration cycle. For this reason, the hydroxyl value of the ester is preferably 10 mgKOH/g or lower, and more preferably 5 mgKOH/g or lower. Note that the hydroxyl value in the present invention means a hydroxyl value measured according to the method of Japanese Industrial Standard (JIS) K 0070: 1992.

The ester according to the present invention can be produced, for example, by an ordinary esterification method (for example, a method described in Japanese Patent Application Publication No. 2001-107067 or the like) using pentaerythritol and/or dipentaerythritol and 2-propylheptanoic acid. The mixture of an ester between pentaerythritol and 2-propylheptanoic acid and an ester between dipentaerythritol and 2-propylheptanoic acid may also be produced by producing the ester between pentaerythritol and 2-propylheptanoic acid and the ester between dipentaerythritol and 2-propylheptanoic acid each independently, and mixing the esters with each other. In addition, the mixing ratio of the two esters in the mixture may be any.

2-Propylheptanoic acid can be produced by a known method, for example, by conducting aldol condensation of n-valeraldehyde in the presence of an alkali catalyst, and hydrogenating the double bond moiety of the obtained unsaturated aldehyde, followed by oxidization according to the method described in Japanese Patent Application Publication No. Hei 8-109299. Here, n-valeraldehyde can be obtained as a commercially available product, or can be obtained by a known method, for example, by a method based on a hydroformylation reaction of 1-butene (which contains isomers such as 2-butene and isobutene in some cases) serving as a raw material. The n-valeraldehyde obtained by the hydroformylation reaction contains isomers derived from the raw material and isomers due to the reaction in some cases. When 2-propylheptanoic acid is produced by using such n-valeraldehyde as a raw material through the aldol condensation reaction, the 2-propylheptanoic acid contains aldol condensate derivatives derived from these isomers (for example, 2-(1-methylethyl)heptanoic acid, 4-methyl-2-propylhexanoic acid, 5-methyl-2-propylhexanoic acid, 4-methyl-2-(1-methylethyl)hexanoic acid, and the like) in some cases. The refrigerating machine oil of the present invention may contain an impurity amount of esters derived from these aldol condensate derivatives, unless the excellent properties such as lubricity, thermal and chemical stability, and miscibility with refrigerant in the presence of the HFO-1234ze refrigerant are impaired. In addition, other methods for producing 2-propylheptanoic acid include a method based on the pentene dimerization and subsequent oxidization described in DE10239134 and the like.

The refrigerating machine oil of the present invention may be a refrigerating machine oil consisting of only the ester according to the present invention, or may be a refrigerating machine oil comprising the ester according to the present invention and an additional lubricant base oil(s). Moreover, if necessary, the refrigerating machine oil of the present invention may comprise additive(s) for a lubricant oil.

Examples of the additional lubricant base oil include mineral oil, synthetic base oil, and the like.

Examples of the mineral oil include paraffinic-base crude oil, intermediate-base crude oil, naphthenic-base crude oil, and the like. In addition, refined oil obtained by refining these oils by distillation or the like can also be used.

Examples of the synthetic base oil include poly-α-olefins (polybutene, polypropylene, α-olefin oligomers having 8 to 14 carbon atoms, and the like), aliphatic esters other than the ester according to the present invention (fatty acid monoesters, fatty acid esters of polyols, aliphatic polybasic acid esters, and the like), aromatic esters (aromatic monoesters, aromatic esters of polyols, aromatic polybasic acid esters, and the like), polyalkylene glycols, polyvinyl ethers, polycarbonates, alkylbenzenes, and the like. Here, examples of the fatty acid esters of polyols among the aliphatic esters other than the ester according to the present invention include an ester between neopentyl glycol and 2-ethylhexanoic acid, an ester between pentaerythritol and pentanoic acid, heptanoic acid, and 3,5,5-trimethylhexanoic acid, an ester between pentaerythritol and 2-ethylhexanoic acid, an ester between pentaerythritol and 2-ethylhexanoic acid and 3,5,5-trimethylhexanoic acid, an ester between pentaerythritol and 3,5,5-trimethylhexanoic acid, an ester between dipentaerythritol and pentanoic acid, heptanoic acid, and 3,5,5-trimethylhexanoic acid, an ester between dipentaerythritol and 2-ethylhexanoic acid, mixtures of two or more selected from the above-described esters, and the like.

In the refrigerating machine oil of the present invention, the content of the additional base oil is not particularly limited, and is preferably 30% by weight or less, more preferably 20% by weight or less, and most preferably 10% by weight or less based on the total amount of the refrigerating machine oil, from the viewpoints of the lubricity, the thermal and chemical stability, and the miscibility with refrigerant in the presence of the HFO-1234ze refrigerant.

Examples of the additive for a lubricant oil include antioxidant, wear-reducing agent (anti-wear agent, anti-seizure agent, extreme pressure agent, and the like), friction modifier, acid scavenger, metal deactivator, rust preventive agent, anti-foaming agent, and the like. The content of each of these additives is preferably 0.001 to 5% by weight based on the total amount of the refrigerating machine oil.

Examples of the antioxidant include phenol-based antioxidants such as 2,6-di-tert-butyl-4-methylphenol, 2,6-di-tert-butyl-4-ethylphenol, and 4,4'-methylenebis(2,6-di-tert-butylphenol), amine-based antioxidants such as phenyl-α-naphthylamine and N,N'-diphenyl-p-phenylenediamine, and the like.

Examples of the wear-reducing agent include phosphorus-based extreme pressure agents such as phosphoric acid esters, phosphorothioic acid esters, acidic phosphoric acid esters, phosphite esters, and amine salts of acidic phosphoric acid esters.

Examples of the phosphoric acid esters include tributyl phosphate, tripentyl phosphate, trihexyl phosphate, triheptyl phosphate, trioctyl phosphate, tris(2-ethylhexyl)phosphate, trinonyl phosphate, tridecyl phosphate, triundecyl phosphate, tridodecyl phosphate, tritridecyl phosphate, tritetradecyl phosphate, tripentadecyl phosphate, trihexadecyl phosphate, triheptadecyl phosphate, trioctadecyl phosphate, trioleyl phosphate, triphenyl phosphate, tricresyl phosphate, dicresyl phenyl phosphate, cresyl diphenyl phosphate, trixylenyl phosphate, dixylenyl phenyl phosphate, xylenyl diphenyl phosphate, and the like.

Examples of the phosphorothioic acid esters include tributyl phosphorothioate, tripentyl phosphorothioate, trihexyl phosphorothioate, triheptyl phosphorothioate, trioctyl phosphorothioate, trinonyl phosphorothioate, tridecyl phosphorothioate, triundecyl phosphorothioate, tridodecyl phosphorothioate, tritridecyl phosphorothioate, tritetradecyl phosphorothioate, tripentadecyl phosphorothioate, trihexadecyl phosphorothioate, triheptadecyl phosphorothioate, trioctadecyl phosphorothioate, trioleyl phosphorothioate, triphenyl phosphorothioate, tricresyl phosphorothioate, dicresyl phenyl phosphorothioate, cresyl diphenyl phosphorothioate, trixylenyl phosphorothioate, dixylenyl phenyl phosphorothioate, xylenyl diphenyl phosphorothioate, and the like.

Examples of the acidic phosphoric acid esters include monobutyl acid phosphate, monopentyl acid phosphate, monohexyl acid phosphate, monoheptyl acid phosphate, monooctyl acid phosphate, monononyl acid phosphate, monodecyl acid phosphate, monoundecyl acid phosphate, monododecyl acid phosphate, monotridecyl acid phosphate, monotetradecyl acid phosphate, monopentadecyl acid phosphate, monohexadecyl acid phosphate, monoheptadecyl acid phosphate, monooctadecyl acid phosphate, monooleyl acid phosphate, dibutyl acid phosphate, dipentyl acid phosphate, dihexyl acid phosphate, diheptyl acid phosphate, dioctyl acid phosphate, dinonyl acid phosphate, didecyl acid phosphate, diundecyl acid phosphate, didodecyl acid phosphate, ditridecyl acid phosphate, ditetradecyl acid phosphate, dipentadecyl acid phosphate, dihexadecyl acid phosphate, diheptadecyl acid phosphate, dioctadecyl acid phosphate, dioleyl acid phosphate, and the like.

Examples of the phosphite esters include triethyl phosphite, tributyl phosphite, tris(2-ethylhexyl)phosphite, triisooctyl phosphite, tridecyl phosphite, tridodecyl phosphite, trioctadecyl phosphite, trioleyl phosphite, triphenyl phosphite, tricresyl phosphite, tris(nonylphenyl)phosphite, diphenyl isodecyl phosphite, and the like.

Examples of the amine salts of acidic phosphoric acid esters include salts of the above-described acidic phosphoric acid esters with amines such as methylamine, ethylamine, propylamine, butylamine, pentylamine, hexylamine, heptylamine, octylamine, dimethylamine, diethylamine, dipropylamine, dibutylamine, dipentylamine, dihexylamine, diheptylamine, dioctylamine, trimethylamine, triethylamine, tripropylamine, tributylamine, tripentylamine, trihexylamine, triheptylamine, trioctylamine, and the like.

Examples of the acid scavenger include phenyl glycidyl ethers such as phenyl glycidyl ether, butylphenyl glycidyl ether, i-butylphenyl glycidyl ether, sec-butylphenyl glycidyl ether, tert-butylphenyl glycidyl ether, pentylphenyl glycidyl ether, hexylphenyl glycidyl ether, heptylphenyl glycidyl ether, octylphenyl glycidyl ether, nonylphenyl glycidyl ether, and decylphenyl glycidyl ether; alkyl glycidyl ethers such as 2-ethylhexyl glycidyl ether, decyl glycidyl ether, undecyl glycidyl ether, dodecyl glycidyl ether, tridecyl glycidyl ether, and tetradecyl glycidyl ether; polyol polyglycidyl ethers such as neopentyl glycol diglycidyl ether, trimethylolpropane triglycidyl ether, pentaerythritol tetraglycidyl ether, 1,6-hexanediol diglycidyl ether, sorbitol polyglycidyl ether, polyalkylene glycol monoglycidyl ethers, and polyalkylene glycol diglycidyl ethers; glycidyl esters such as glycidyl 2-ethylhexanoate, glycidyl 3,5,5-trimethylhexanoate, glycidyl decanoate, glycidyl neodecanoate, glycidyl dodecanoate, glycidyl tetradecanoate, glycidyl benzoate, glycidyl acrylate, and glycidyl methacrylate; alkyloxiranes such as 1,2-epoxybutane, 1,2-epoxypentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxytridecane, 1,2-epoxytetradecene, 1,2-epoxypentadecane, 1,2-epoxyhexadecane, 1,2-epoxyheptadecane, 1,2-epoxyoctadecane, 1,2-epoxynonadecane, and 1,2-epoxyicosane; alicyclic epoxy compounds such as 1,2-epoxycyclopentane, 1,2-epoxycyclohexane, 3,4-epoxycyclohexylmethyl 3,4-epoxycyclohexane carboxylate, bis(3,4-epoxycyclohexylmethyl) adipate, exo-2,3-epoxynorbornane, bis(3,4-epoxy-6-methylcyclohexylmethyl) adipate, 2-(7-oxabicyclo[4.1.0]heptan-3-yl)-spiro[1,3-dioxane-5,3'-[7]oxabicyclo[4.1.0]heptane], 1-methyl-4-(2-methyloxiran-2-yl)-7-oxabicyclo[4.1.0]heptane, and 3-(1,2-epoxyethyl)-7-oxabicyclo[4.1.0]heptane; carbodiimides such as diisopropylcarbodiimide, bis(dipropylphenyl)carbodiimide, and bis(dibutylphenyl)carbodiimide; and the like.

Examples of the metal deactivator include benzotriazole and the like. Examples of the anti-foaming agent include dimethylsiloxane and the like.

The kinematic viscosity of the refrigerating machine oil of the present invention means a kinematic viscosity measured by using a Cannon-Fenske viscometer according to the method of Japanese Industrial Standard (JIS) K 2283:2000.

Meanwhile, the water content in the refrigerating machine oil of the present invention is not particularly limited, and is preferably 200 ppm or less, more preferably 100 ppm or less, further preferably 70 ppm or less, and most preferably 50 ppm or less, based on the total amount of the refrigerating machine oil. Especially when the refrigerating machine oil is used for a hermetic refrigerating machine, the water content is required to be low from the viewpoints of influences on the thermal and chemical stability and the electrical insulating properties of the refrigerating machine oil.

In addition, the acid number of the refrigerating machine oil of the present invention is not particularly limited, and is preferably 0.1 mgKOH/g or lower, and more preferably 0.05 mgKOH/g or lower. A high acid number of the refrigerating machine oil leads to promotion of the corrosion of the metal used in the refrigerating machine or piping and also promotion of the decomposition of the ester contained in the refrigerating machine oil of the present invention. Hence, the acid number is required to be low. Note that the acid number in the present invention means an acid number measured according to the method of Japanese Industrial Standard (JIS) K 2501:2003.

The electrical insulating properties are generally expressed by the volume resistivity. The volume resistivity of the refrigerating machine oil of the present invention is not particularly limited, and is preferably $1.0 \times 10^{12}$ Ω·cm or higher, more preferably $1.0 \times 10^{13}$ Ω·cm or higher, and most preferably $1.0 \times 10^{14}$ Ω·cm or higher. Especially when the refrigerating machine oil is used for a hermetic refrigerating machine, high electrical insulating properties tend to be necessary. Note that the volume resistivity in the present invention means a value at 30° C. measured according to the method of Japanese Industrial Standard (JIS) C 2101:1999.

In addition, the pour point of the refrigerating machine oil of the present invention is not particularly limited, and is preferably −10° C. or below, more preferably −30° C. or below, and most preferably −40° C. or below. Note that the pour point in the present invention means a value measured according to the method of Japanese Industrial Standard (JIS) K 2269:1987. Moreover, when the refrigerating machine oil of the present invention is used under a low-temperature environment in a cold district or the like, the refrigerating machine oil has to have such properties (low-temperature properties) that solidification or precipitation does not occur at about −20° C., in addition to the low pour point. The pour points of base oils 1 to 4 (described later) of Examples 1 to 4, which are embodiments of the refrigerating machine oil of the present invention, were −40° C. or below. On the other hand, the pour point of a base oil 6 (described later) of Comparative Example 2 was 0° C. In addition, the base oils 1 to 4 did not generate solidification or precipitation, when they were allowed to stand at −20° C. for 24 hours. It can be said that they have good low-temperature properties.

In some cases, 2-propylheptanoic acid, which is a raw material of the ester according to the present invention, contains, as impurities, compounds having unsaturated bonds produced during the production of the 2-propylheptanoic acid. When the ester according to the present invention contains the compounds, an acid may be generated because of the oxidative decomposition of the unsaturated bonds, so that the thermal and chemical stability tends to deteriorate. For this reason, the iodine value of the ester according to the present invention is preferably 0.1 (Ig/100 g) or lower, more preferably 0.07 (Ig/100 g) or lower, and most preferably 0.05 (Ig/100 g) or lower. Note that the iodine value in the present invention means an iodine value measured by the same method as in Japanese Industrial Standard (JIS) K 0070:1992, except that the amount of the sample is 20 g.

HFO-1234ze has a molecular structure in which an unsaturated bond exists. Hence, when oxygen is contained, oxidative decomposition of HFO-1234ze occurs to generate an acid. The generated acid increases the acid number of the refrigerating machine oil, and promotes the corrosion of the metal and the decomposition of the ester contained in the refrigerating machine oil as mentioned above. Accordingly, a refrigerating machine oil used in combination with the HFO-1234ze refrigerant is required to have high thermal and chemical stability. Here, the thermal and chemical stability of a refrigerating machine oil can be evaluated, for example, as follows. Specifically, the refrigerant, the refrigerating machine oil, metals (iron, copper, aluminum, and the like) used for the refrigerating machine, and optionally water, air, and the like, which are added assuming that they may be contained as contaminants in the refrigerant-circulation cycle, are sealed in a pressure-resistant vessel. Then, an accelerated aging test is conducted by applying heat, and the state of the sealed materials is observed after the test.

In addition, the decomposition of the ester is promoted when an active metal surface formed at a sliding portion in a refrigerant compressor acts as a catalyst. Hence, a metal deactivator (benzotriazole or the like) is added to the refrigerating machine oil in some cases. To inhibit the decomposition of the ester, it is important that the metal deactivator should be readily adsorbed on the metal surface. The degree of the adsorption properties of a metal deactivator on a metal surface can be determined, for example, by reference to the method described in "MASATSUCHOSEIZAI NO BUN-SHISEKKEI (Molecule Design of Friction Modifiers) (Second Report)", Journal of Japanese Society of Tribologists, Vol. 38, No. 3 (1993), pp 247-253 or the like. When a metal deactivator is contained in the refrigerating machine oil of the present invention, the metal deactivator exhibits excellent adsorption properties on a metal surface.

A refrigerating machine oil used in combination with the HFO-1234ze refrigerant is required to have excellent miscibility with the refrigerant. If the miscibility with the refrigerant is poor, phase separation of the refrigerant and the refrigerating machine oil occurs, and the refrigerating machine oil discharged from a refrigerant compressor builds up in a refrigerant-circulation cycle. This may cause problems such as lubrication failure in the refrigerant compressor. The miscibility with a refrigerant is generally expressed by using the two-phase separation temperature. It can be said that the lower the two-phase separation temperature, the better the miscibility on a low-temperature side. When the refrigerating machine oil of the present invention is mixed at 10% by weight with the HFO-1234ze refrigerant, the two-phase separation temperature is preferably −10° C. or below. Note that the two-phase separation temperature in the present invention means a value measured by using HFO-1234ze as the refrigerant according to the method of Japanese Industrial Standard (JIS) K 2211:2009.

A refrigerating machine oil used in combination with the HFO-1234ze refrigerant is required to have excellent lubricity. The lubricity includes, for example, wear-reducing properties (antiwear properties), extreme pressure properties, friction-reducing properties, and the like. The lubricity of a refrigerating machine oil in the presence of a refrigerant can be evaluated, for example, by a friction and wear test using a block-on-ring friction and wear testing machine (manufactured by FALEX Corporation) of a sealed pressurization type in which a sliding portion is housed in a pressure-resistant vessel by reference to ASTM D2714.

In a refrigerant-circulation cycle of a refrigerating machine or the like, the refrigerating machine oil of the present invention is present generally in the form of a working fluid composition for a refrigerating machine mixed with the HFO-1234ze refrigerant. The mixing ratio of the refrigerating machine oil and the refrigerant in the fluid composition is not particularly limited, and the ratio of the refrigerating machine oil of the present invention is preferably 1 to 1000 parts by weight, and more preferably 2 to 800 parts by weight, relative to 100 parts by weight of the refrigerant.

The refrigerating machine oil and the working fluid composition for a refrigerating machine of the present invention can be used preferably for room air conditioners, packaged air conditioners, automobile air conditioners, dehumidifiers, refrigerators, freezers, refrigerator-freezers, vending machines, showcases, refrigerating machines installed in chemical plants, and the like.

EXAMPLES

Hereinafter, the present invention will be described more specifically based on Examples and Comparative Examples; however, the present invention is not limited to Examples below.

Examples 1 to 4 and Comparative Examples 1 to 6

In each of Examples 1 to 4 and Comparative Examples 1 to 6, evaluation tests described later were carried out by using the corresponding one of base oils 1 to 10 shown below as a refrigerating machine oil. Table 1 shows various properties of the obtained refrigerating machine oils.

(Base Oils)

Base oil 1: an ester between pentaerythritol and 2-propylheptanoic acid

Base oil 2: an ester between dipentaerythritol and 2-propylheptanoic acid

Base oil 3: a mixture of the base oil 1 and the base oil 2 (mixing ratio (weight ratio):base oil 1/base oil 2=75/25)

Base oil 4: a mixture of the base oil 1 and the base oil 2 (mixing ratio (weight ratio):base oil 1/base oil 2=39/61)

Base oil 5: an ester between pentaerythritol and 3,5,5-trimethylhexanoic acid

Base oil 6: an ester between pentaerythritol and 2-ethylhexanoic acid

Base oil 7: an ester between pentaerythritol and a carboxylic acid mixture of 2-ethylhexanoic acid and 3,5,5-trimethylhexanoic acid (the ratio of the acids introduced to the ester (mole ratio):2-ethylhexanoic acid/3,5,5-trimethylhexanoic acid=49/51)

Base oil 8: an ester between dipentaerythritol and a carboxylic acid mixture of 2-ethylhexanoic acid and 3,5,5-trimethylhexanoic acid (the ratio of the acids introduced to the ester (mole ratio):2-ethylhexanoic acid/3,5,5-trimethylhexanoic acid=49/51)

Base oil 9: an ester between dipentaerythritol and 2-ethylhexanoic acid

Base oil 10: a mixture of the base oil 6 and the base oil 9 (mixing ratio (weight ratio):base oil 6/base oil 9=75/25)

Production Examples

Production of 2-Propylheptanoic Acid (1) Production of 2-Propyl-2-heptenal

To a reactor equipped with a dropping funnel and a condenser, 14 g of sodium hydroxide (0.3 mol, manufactured by Kanto Chemical Co., Inc.) and 340 mL of water were added, and 1478 g of n-valeraldehyde (17.2 mol, manufactured by Toyo Gosei Co., Ltd) placed in the dropping funnel was added dropwise over 4.5 hours with stirring at 80° C. After stirring at 90° C. for further 2 hours, the aqueous layer was removed from the reaction product. Subsequently, the reaction product was purified by distillation (b.p.: 100° C./1.3 kPa) to obtain 1238 g of 2-propyl-2-heptenal.

(2) Production of 2-Propylheptanal

In an autoclave, 431 g of 2-propyl-2-heptenal and 2 g of 5% Pd carbon powder (56% wet, manufactured by N.E. CHEMCAT Corporation) were placed, and stirred at 75° C. for 4.5 hours under a hydrogen pressure of 1.5 MPa. Subsequently, the reaction product was filtered through a membrane filter (PTFE, 0.5 μm) to obtain 430 g of 2-propylheptanal.

(3) Production of 2-Propylheptanoic Acid

To a reactor, 25 g of a 25% aqueous sodium hydroxide solution and 1232 g of 2-propylheptanal were added, followed by air bubbling at 40° C. for 20 hours. The air bubbling was switched to nitrogen bubbling, and the mixture was stirred at 120° C. for 5 hours to obtain 1300 g of a crude product of 2-propylheptanoic acid. The obtained crude product (1300 g) of 2-propylheptanoic acid was distilled. After 186 g of low-boiling point components (80° C./0.8 kPa to 140° C./0.4 kPa) were removed, a main fraction (b.p.: 133° C./0.2 kPa to 138° C./0.3 kPa) was obtained. Thus, 958 g of 2-propylheptanoic acid was obtained.

$^1$H-NMR (GSX-400 manufactured by JEOL Ltd. (400 MHz), CDCl$_3$, δ ppm); 0.88 (t, 3H), 0.92 (t, 3H), 1.29 to 1.50 (m, 10H), 1.58 to 1.67 (m, 2H), 2.33 to 2.40 (m, 1H)

[Production of Base Oil 1]

To a reactor equipped with a Dean-Stark trap, 155 g of pentaerythritol (1.1 mol, manufactured by Koei-Perstorp Co., Ltd., Product Name: Pentarit-S) and 944 g of 2-propylheptanoic acid (5.5 mol, Production Example) were added, and the mixture was degassed by nitrogen bubbling with stirring under a reduced pressure of 27 kPa at room temperature for 15 minutes.

Subsequently, the mixture was stirred at 216° C. to 252° C. for 25 hours under atmospheric pressure with nitrogen bubbling. After the reaction, the reaction product was stirred under a reduced pressure of 0.7 to 1.0 kPa at 232 to 241° C. for 3 hours to distill off the unreacted carboxylic acid in the reaction product. The reaction product was washed at 90° C. for 2 hours with 270 mL of an aqueous alkaline solution containing sodium hydroxide in an amount of moles which was twice the acid number of the reaction product. Subsequently, the reaction product was washed with 270 mL of water at 90° C. for 1 hour three times. Subsequently, the reaction product was stirred with nitrogen bubbling under a reduced pressure of 0.6 kPa at 90° C. for 0.5 hours to dry the reaction product.

To the reaction product, 5.2 g of an adsorbent (manufactured by Kyowa Chemical Industry Co., Ltd., Product Name: KYOWAAD 500) and 17.2 g of activated carbon (manufactured by Japan EnviroChemicals, Limited, Product Name: SHIRASAGI P) were added. With nitrogen bubbling, the reaction product was stirred under a reduced pressure of 0.4 kPa at 90° C. for 1 hour, and then filtered under a nitrogen atmosphere by using a filter aid (manufactured by Showa Chemical Industry Co., Ltd., Product Name: Radiolite #500) dried under reduced pressure in advance. Thus, 764 g of the base oil 1 was obtained. The base oil 1 had a water content of 42 ppm and an iodine value of 0.04 (Ig/100 g).

[Production of Base Oil 2]

A base oil 2 was obtained by conducting the same operations as in Production Example of the base oil 1, except that dipentaerythritol (manufactured by Koei-Perstorp Co., Ltd., Product Name: Di-Pentarit) was used instead of pentaerythritol and that the mole ratio of the dipentaerythritol and the 2-propylheptanoic acid used (the ratio of dipentaerythritol/2-propylheptanoic acid) was set to 1/7.2. The base oil 2 had a water content of 47 ppm and an iodine value of 0.05 (Ig/100 g).

[Production of Base Oil 3]

A base oil 3 was obtained by mixing the base oil 1 (150 g) with the base oil 2 (50 g) under a nitrogen atmosphere at room temperature by using a mixer. The base oil 3 had a water content of 48 ppm and an iodine value of 0.05 (Ig/100 g).

[Production of Base Oil 4]

A base oil 4 was obtained by mixing the base oil 1 (78 g) with the base oil 2 (122 g) under a nitrogen atmosphere at room temperature by using a mixer. The base oil 4 had a water content of 50 ppm and an iodine value of 0.05 (Ig/100 g).

[Production of Base Oil 5]

A base oil 5 was obtained by conducting the same operations as in Production Example of the base oil 1, except that 3,5,5-trimethylhexanoic acid (manufactured by KH Neochem Co., Ltd.) was used instead of 2-propylheptanoic acid and that the mole ratio of the pentaerythritol and the 3,5,5-trimethylhexanoic acid used (the ratio of pentaerythritol/3,5,5-trimethylhexanoic acid) was set to 1/4.8.

[Production of Base Oil 6]

A base oil 6 was obtained by conducting the same operations as in Production Example of the base oil 1, except that 2-ethylhexanoic acid (manufactured by KH Neochem Co., Ltd.) was used instead of 2-propylheptanoic acid, and that the mole ratio of the pentaerythritol and the 2-ethylhexanoic acid used (the ratio of pentaerythritol/2-ethylhexanoic acid) was set to 1/4.8.

[Production of Base Oil 7]

A base oil 7 was obtained by conducting the same operations as in Production Example of the base oil 1, except that a carboxylic acid mixture of 2-ethylhexanoic acid (manufactured by KH Neochem Co., Ltd.) and 3,5,5-trimethylhexanoic acid (manufactured by KH Neochem Co., Ltd.) was used instead of 2-propylheptanoic acid and that the mole ratio of the pentaerythritol, the 2-ethylhexanoic acid, and the 3,5,5-trimethylhexanoic acid used (the ratio of pentaerythritol/2-ethylhexanoic acid/3,5,5-trimethylhexanoic acid) was set to 1/2.5/2.3.

$^1$H-NMR measurement was conducted (GSX-400 manufactured by JEOL Ltd. (400 MHz), CDCl$_3$), and the acid introduction ratio (mole ratio) of 2-ethylhexanoic acid to 3,5,5-trimethylhexanoic acid in the base oil 7 was calculated by the following formula:

2-Ethylhexanoic acid/3,5,5-Trimethylhexanoic acid=
(Integrated value of peak $A$−Integrated value of peak $B$)/Integrated value of peak $B$.

Here, the peak A is equivalent to the total of the peak of the one hydrogen atom on the methine group at α-position to the carbonyl group of 2-ethylhexanoic acid and one of the peaks of the hydrogen atoms on the methylene group at α-position to the carbonyl group of 3,5,5-trimethylhexanoic acid, the one peak being attributable to one hydrogen atom and being located on the lower-magnetic field side. The peak B is equivalent to the other one of the peaks of the hydrogen atoms on the methylene group at α-position to the carbonyl group of 3,5,5-trimethylhexanoic acid, the other one peak being attributable to one hydrogen atom and being located on the higher-magnetic field side.

[Production of Base Oil 8]

A base oil 8 was obtained by conducting the same operations as in Production Example of the base oil 1, except that dipentaerythritol (manufactured by Koei-Perstorp Co., Ltd., Product Name: Di-Pentarit) was used instead of pentaerythritol, that a carboxylic acid mixture of 2-ethylhexanoic acid (manufactured by KH Neochem Co., Ltd.) and 3,5,5-trimethylhexanoic acid (manufactured by KH Neochem Co., Ltd.) was used instead of 2-propylheptanoic acid, and that the mole ratio of the dipentaerythritol, the 2-ethylhexanoic acid, and the 3,5,5-trimethylhexanoic acid used (the ratio of dipentaerythritol/2-ethylhexanoic acid/3,5,5-trimethylhexanoic acid) was set to 1/3.6/3.6.

$^1$H-NMR measurement was conducted (GSX-400 manufactured by JEOL Ltd. (400 MHz), CDCl$_3$), and the acid introduction ratio (mole ratio) of 2-ethylhexanoic acid to 3,5,5-trimethylhexanoic acid in the base oil 8 was calculated by the following formula:

2-Ethylhexanoic acid/3,5,5-Trimethylhexanoic acid=
(Integrated value of peak $A$−Integrated value of peak $B$)/Integrated value of peak $B$.

Here, the peak A and the peak B are as defined above.

[Production of Base Oil 9]

A base oil 9 was obtained by conducting the same operations as in Production Example of the base oil 1, except that dipentaerythritol (manufactured by Koei-Perstorp Co., Ltd., Product Name: Di-Pentarit) was used instead of pentaerythritol, that 2-ethylhexanoic acid (manufactured by KH Neochem Co., Ltd.) was used instead of 2-propylheptanoic acid, and that the mole ratio of the dipentaerythritol and the 2-ethylhexanoic acid used (the ratio of dipentaerythritol/2-ethylhexanoic acid) was set to 1/9.0.

[Production of Base Oil 10]

A base oil 10 was obtained by mixing the base oil 6 (150 g) with the base oil 9 (50 g) under a nitrogen atmosphere at room temperature by using a mixer.

Refrigerating machine oils of Examples 1 to 4 and Comparative Examples 1 to 6 were subjected to evaluation tests shown below.

(Evaluation of Miscibility with Refrigerant)

The two-phase separation temperature of each refrigerating machine oil was measured according to the method of JIS K 2211:2009. In a pressure resistant glass tube, 0.4 g of the refrigerating machine oil and 3.6 g of HFO-1234ze (manufactured by Honeywell International Inc.) were sealed, and this mixture was cooled from 30° C. at a rate of 0.5° C./min. The temperature at which the mixture separated into two phases or turned cloudy was regarded as the two-phase separation temperature. Table 1 shows the results.

(Evaluation of Lubricity)

The lubricity of each refrigerating machine oil was evaluated by a friction and wear test by reference to ASTM D2714. The friction and wear test was carried out as follows by using a block-on-ring friction and wear testing machine (manufactured by FALEX Corporation) of a sealed pressurization type in which a sliding portion was housed in a pressure-resistant vessel. Specifically, 100 ml of the refrigerating machine oil was placed in the pressure-resistant vessel. Then, while HFO-1234ze (manufactured by Honeywell International Inc.) was introduced into a gas phase portion with the absolute pressure being kept at 600 kPa, the friction and wear test was conducted under the following conditions. After the friction and wear test, the wear scar on the test block was observed. A case where no seizure was observed was evaluated as "Good", while a case where seizure was observed was evaluated as "Poor". Here, the seizure refers to a state where welding occurred on the friction surface, creating a rugged surface. In addition, the widths of the wear scars of the test blocks in which no seizure was observed were measured. Table 1 shows the results.

<Conditions>

Test materials: Test Rings (FALEX Type S-10), Test Blocks (FALEX Type H-60)

Initial temperature of test: 60° C.

Duration of test: 1 hour

Sliding speed: 0.5 m/s

Load: 800 N

Absolute pressure of refrigerant atmosphere: 600 kPa (Evaluation of Thermal and Chemical Stability)

The thermal and chemical stability of each refrigerating machine oil was evaluated according to the method of JIS K 2211:2009. In a 200 ml autoclave, 30 g of the refrigerating machine oil whose water content was adjusted to 1000 ppm and catalysts (wires of iron, copper, and aluminum) were placed. The content in the autoclave was degassed under reduced pressure with a vacuum pump. Then, 30 g of HFO-1234ze (manufactured by Honeywell International Inc.) and 20 ml of air were further sealed. The entirety of the autoclave was heated at 175° C. for 168 hours, and after that the acid number of the refrigerating machine oil was measured. Table 1 shows the results.

As is apparent from the results shown in Table 1, it can be seen that, when used in combination with an HFO-1234ze refrigerant, the refrigerating machine oil of each of Examples 1 to 4 was excellent in miscibility with the refrigerant, lubricity, and thermal and chemical stability. On the other hand, seizure was observed in the evaluation of the lubricity of each of the refrigerating machine oils of Comparative Examples 1 to 3, 5, and 6. In the case of the refrigerating machine oil of Comparative Example 4, seizure was not observed, but the width of the wear scar was larger than in the cases of the refrigerating machine oils of Examples 1 to 4. It can be said that these refrigerating machine oils are poorer in antiwear properties than the refrigerating machine oils of Examples 1 to 4. In addition, in the evaluation of the thermal and chemical stability, the refrigerating machine oil of Comparative Example 4 underwent a larger increase in acid number after heating than the refrigerating machine oils of Examples 1 to 4. Hence, it can be said that the refrigerating machine oil of Comparative Example 4 was poorer in thermal and chemical stability than the refrigerating machine oils of Examples 1 to 4.

Refrigerating machine oils were prepared by mixing benzotriazole with the base oils of Examples 1 to 4 and Comparative Example 3, and subjected to the evaluation test shown below.

(Evaluation of Adsorption Properties of Benzotriazole)

1) Method for $^1$H-NMR Measurement

Measuring apparatus: JNM-ECA500 (500 MHz) manufactured by JEOL Ltd.

Sample preparation: Measurement sample (0.1 g) was mixed with 1 g of $CDCl_3$ and 0.04 to 0.05 g of $D_2O$ Number of scans: 128

2) Evaluation of Adsorption Properties

Adsorption properties of benzotriazole in each refrigerating machine oil containing benzotriazole on a metal surface were evaluated.

Refrigerating machine oils were prepared by dissolving benzotriazole (manufactured by Sigma-Aldrich Co. LLC) in the base oils 1 to 4 and Comparative Example 3 at a concentration of 0.5% by weight. The refrigerating machine oils were subjected to $^1$H-NMR measurement, and the ratio before adsorption was calculated by the following formula.

Ratio before adsorption=Integrated value of peak C/Integrated value of peak D

TABLE 1

| | | Ex. 1 | Ex. 2 | Ex. 3 | Ex. 4 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|---|---|---|
| Base oil No. | | 1 | 2 | 3 | 4 | 5 | 6 | 7 | 8 | 9 | 10 |
| Acid number [mgKOH/g] | | 0.006 | 0.002 | 0.005 | 0.004 | 0.003 | 0.003 | 0.002 | 0.012 | 0.004 | 0.004 |
| Hydroxyl value [mgKOH/g] | | 0.7 | 1.9 | 1.0 | 1.4 | 0.8 | 2.2 | 1.0 | 0.1 | 0.3 | 1.6 |
| Kinematic viscosity [mm$^2$/sec] | 40° C. | 54.3 | 154.9 | 68.2 | 100.8 | 109.9 | 44.1 | 67.7 | 241.2 | 139.5 | 56.8 |
| | 100° C. | 7.7 | 16.3 | 9.0 | 12.2 | 11.3 | 6.2 | 8.4 | 19.8 | 14.3 | 7.5 |
| Miscibility with refrigerant | Two-phase separation temperature [° C.] | <−50 | −30 | −48 | −40 | <−50 | <−50 | <−50 | <−50 | <−50 | <−50 |
| Lubricity | Seizure | Good | Good | Good | Good | Poor | Poor | Poor | Good | Poor | Poor |
| | Width of wear scar [mm] | 0.74 | 0.79 | 0.72 | 0.75 | — | — | — | 0.96 | — | — |
| Thermal and chemical stability | Acid number [mgKOH/g] | 0.16 | 0.18 | 0.13 | 0.15 | 0.98 | 0.19 | 0.33 | 0.61 | 0.22 | 0.20 |

Here, the peak C is attributable to the hydrogen atoms on the carbon atoms at positions 5 and 6 of benzotriazole, whereas the peak D is equivalent to the peak of the hydrogen atoms on the methylene groups of pentaerythritol, one of the two peaks attributable to the hydrogen atoms on the methylene groups of dipentaerythritol, the one peak appearing on the lower magnetic field side, or the total of the peak of the hydrogen atoms on the methylene groups of pentaerythritol and one of the two peaks attributable to the hydrogen atoms on the methylene groups of dipentaerythritol, the one peak appearing on the lower magnetic field side.

To a 20 ml sample bottle, 10 g of the refrigerating machine oil and 5 g of iron oxide (manufactured by Sigma-Aldrich Co. LLC, particle size <5 μm) were added, and the sample bottle was heated in a water bath at 60° C. for 30 minutes. Subsequently, after stirring with a mixer, the sample bottle was allowed to stand at room temperature for 30 minutes. Further, iron oxide was sedimented by centrifugation. The supernatant was subjected to $^1$H-NMR measurement, and the ratio after adsorption was calculated by the following formula:

Ratio after adsorption=Integrated value of peak $C$/Integrated value of peak $D$ Here, the peak C and the peak D are as defined above.

Subsequently, the adsorption ratio of benzotriazole on the iron oxide was calculated by the following formula:

Adsorption ratio (%)=(1−Ratio after adsorption/Ratio before adsorption)×100

The results showed that the refrigerating machine oil of Example 1 achieved an adsorption ratio of 37%, the refrigerating machine oil of Example 2 achieved an adsorption ratio of 32%, the refrigerating machine oil of Example 3 achieved an adsorption ratio of 35%, and the refrigerating machine oil of Example 4 achieved an adsorption ratio of 32%. On the other hand, the refrigerating machine oil of Comparative Example 3 achieved an adsorption ratio of 14%. Benzotriazole, which was a metal deactivator, was more efficiently adsorbed on the metal surface in each of the refrigerating machine oils of Examples 1 to 4 than in the refrigerating machine oil of Comparative Example 3. Hence, it can be said that each of the refrigerating machine oils of Examples 1 to 4 can be effectively used as a refrigerating machine oil for the HFO-1234ze refrigerant and also can be effectively used for a working fluid composition for a refrigerating machine which are required to have high thermal and chemical stability. Here, since the refrigerating machine oil is present at a high ratio in a working fluid composition for a refrigerating machine in a refrigerant compressor, the result of the adsorption ratio presumably reflects the adsorption ratio in the working fluid composition for a refrigerating machine sufficiently.

INDUSTRIAL APPLICABILITY

The present invention makes it possible to provide a refrigerating machine oil for an HFO-1234ze refrigerant which is excellent in miscibility with the refrigerant, lubricity, thermal and chemical stability, and the like, and a working fluid composition for a refrigerating machine using the refrigerating machine oil.

The invention claimed is:

1. A working fluid composition for a refrigerating machine, the working fluid composition comprising:
an ester between a polyol consisting of at least one of pentaerythritol and dipentaerythritol represented by formula (I):

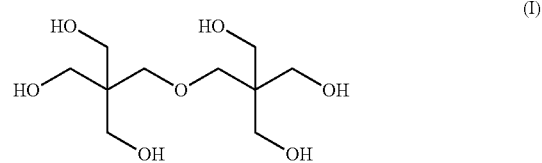

and 2-propylheptanoic acid; and
a refrigerant consisting of HFO-1234ze;
wherein the working fluid composition is free from esters of a polyol and a fatty acid having 5 to 9 carbon atoms.

2. A method for refrigeration, the method comprising:
performing a refrigerant-circulation cycle in a refrigerating machine with a working fluid according to claim 1.

3. The working fluid of claim 1, wherein the working fluid composition is free from esters whose constituent carboxylic acid is other than 2-propylheptanoic acid.

* * * * *